United States Patent
Mattner et al.

(10) Patent No.: US 7,935,252 B2
(45) Date of Patent: May 3, 2011

(54) METHODS OF TREATING ALZHEIMER'S DISEASE WITH AN APHERESIS DEVICE

(75) Inventors: Frank Mattner, Vienna (AT); Walter Schmidt, Vienna (AT)

(73) Assignee: AFFIRIS Forschungs-und Entwicklungs GmbH, Vienna (AT)

( * ) Notice: Subject to any disclaimer, the term of this patent is extended or adjusted under 35 U.S.C. 154(b) by 634 days.

(21) Appl. No.: 10/571,469

(22) PCT Filed: Sep. 13, 2004

(86) PCT No.: PCT/AT2004/000311
§ 371 (c)(1),
(2), (4) Date: Mar. 13, 2006

(87) PCT Pub. No.: WO2005/025651
PCT Pub. Date: Mar. 24, 2005

(65) Prior Publication Data
US 2007/0026029 A1 Feb. 1, 2007

(30) Foreign Application Priority Data
Sep. 12, 2003 (AT) ................ A 1444/2003

(51) Int. Cl.
*A61M 1/10* (2006.01)
*A61K 39/44* (2006.01)
(52) U.S. Cl. .................. 210/195.2; 424/178.1
(58) Field of Classification Search .......... None
See application file for complete search history.

(56) References Cited

U.S. PATENT DOCUMENTS

| 4,409,105 A | 10/1983 | Hayashi et al. |
| 4,770,774 A | 9/1988 | Ida et al. |
| 5,216,127 A | 6/1993 | Hirai et al. |
| 5,604,102 A * | 2/1997 | McConlogue et al. ........ 435/7.1 |
| 5,679,775 A * | 10/1997 | Boos et al. .................... 530/351 |
| 2004/0081657 A1* | 4/2004 | Schenk ..................... 424/185.1 |
| 2007/0010435 A1* | 1/2007 | Frangione et al. ............. 514/12 |
| 2009/0175853 A1* | 7/2009 | Frangione et al. ........ 424/130.1 |

FOREIGN PATENT DOCUMENTS

| EP | 0 236509 | 9/1987 |
| JP | 6-104122 | 4/1994 |
| JP | 2003-523764 | 8/2003 |
| WO | 87/01597 | 4/1987 |
| WO | 95/31727 | 11/1995 |
| WO | 01/62801 | 8/2001 |
| WO | 03/051374 | 6/2003 |
| WO | 2004/056318 | 7/2004 |

OTHER PUBLICATIONS

Alberts 1994. Molecular Biology of the Cell, pp. 104-111.*
Cassel et al. 2001. Demography and Epidemiology of Age-Associated Neuronal Impairment. In: Functional Neurobiology of Aging, pp. 31-50.*
DeMattos 2001 (Proc Natl Acad Sci USA 98:8850-8855).*
Sen 2003 (Anal. Chem. 75:1196-1202).*
Kojima 2001 (J. Biochem. Biophys. Methods 49:241-251).*
Dodart et al. 2002 (Nature Neuroscience 5:452-457).*
U.S. Appl. No. 11/571,970, filed Jan. 11, 2007, Mattner, et al.

* cited by examiner

*Primary Examiner* — Daniel E Kolker
(74) *Attorney, Agent, or Firm* — Oblon, Spivak, McClelland, Maier & Neustadt, L.L.P.

(57) ABSTRACT

The invention relates to an apheresis device for use in the treatment of Alzheimer patients. Said device comprises a solid support with which a flow of blood or plasma can be contacted.

7 Claims, 3 Drawing Sheets

METHODS OF TREATING ALZHEIMER'S DISEASE WITH AN APHERESIS DEVICE

The invention relates to an apheresis device comprising a solid carrier capable of being contacted with the blood or plasma flow.

By apheresis, treatment methods are to be understood whose therapeutic effects are based on the extra-corporeal elimination of pathogenic proteins, protein-bound pathogenic substances, free pathogenic substances or pathogenic cells of the blood. If the pathogenic protein can only be eliminated from the cell-free plasma, the plasma previously is separated from the blood cells by means of a membrane plasma separator (plasma separation) or by means of a haemocentrifuge. In the non-selective plasma exchange (plasmapheresis), the exchanged patient plasma is separated as a whole, wherein besides the pathogens, also all other vital proteins are eliminated. On account of this, substitution of the removed plasma with electrolytes, human albumin or fresh plasma is necessary. In selective plasmapheresis methods, pathogenic proteins can quite specifically be removed from the separated plasma with the help of adsorption, precipitation or filtration, it being possible to re-infuse the plasma without a substantial loss of volume after the removal has been effected. These selective methods have the advantage that one can do without a substitution solution. In selective whole blood apheresis methods, the pathogenic proteins are specifically adsorbed directly from the non-pretreated blood without a previous plasma separation, whereby—in contrast to the plasma separation methods—both the plasma separation and the addition of a substitution solution can be omitted. A further sub-form of apheresis is cytapheresis, in which cells are removed from the blood. With this, leukocytes, erythrocytes, thrombocytes, granulocytes or even stem cells can be recovered selectively.

Even though apheresis (e.g. as plasmapheresis or cytapheresis) currently is mainly used for the recovery of donor plasma (as a plasma pack, for the isolation of various plasma fractions or for the recovery of blood products) apheresis methods are becoming increasingly important in the field of therapy. Currently, a whole series of metabolic illnesses (e.g. (familial) hypercholesterinemia, progressive coronary heart disease with isolated Lp(a) increase, chylomicronemia syndrome, liver failure, . . . ), renal diseases (Goodpasture Syndrome, systemic Lupus erythematodes with lupus nephritis, Wegener's granulomatosis, hemolytic-uremic syndrome, idopathic focal-sclerosing glomerulonephritis, paraproteinemia-associated syndromes, cryoglobulonemic purpura, HLA sensitization in case of kidney transplantation, . . . ) diseases of the nervous system (Myastenia gravis, Guillain-Barre syndrome, chronic demyelinizing polyradiculoneuritis, paraproteinemic polyneuropathy, Lambert-Eaton syndrome, Refsum syndrome, . . . ), diseases of the immune system (rheumatoid arthritis, immune inhibitor hemophilia, pemphigus, . . . ), diseases of the circulatory system and of microcirculation (hyperviscosity syndrome, antiphospholipid antibody syndrome, thrombotic microangiopathy after bone marrow transplantations, age-related macular degeneration, acute hearing loss, peripheral disturbances of microcirculation, idiophathic dilatory cardiomyopathy, transplant vasculopathy after heart transplantation, homozygotic familial hypercholesterinemia, focal segmental glomerulo-sclerosis, hemolytic-uremic syndrome, . . . ), intoxications, acute liver insufficiency, neoplasmas, hyperhydration, thyreotoxicosis, etc., are treated by apheresis methods (cf. Pschyrembel (257. Edition), keyword "Plasmapherese"; www.nephrologie.de/172Apharese.htm).

Alzheimer's Disease (AD) is a progressive neurological disorder, for which currently an effective treatment is not possible. Typical of this disease are cerebral plaques which contain the amyloid β-peptide, and filamentous neuronal structures from the microtubulus-associated TAU protein. Even though amyloid-β and TAU are considered as relevant for the pathogenesis, the most recent research findings seem to suggest that amyloid-β is the major agent in the pathogenesis. Therefore, therapeutic agents are increasingly being developed which are intended to prevent the amyloid-β production, amyloid-β aggregation or the neurotoxic events caused by these aggregates. A comprehensive illustration of the therapeutic strategies for AD hitherto followed is given in the survey article by Wolfe (Nature Reviews Drug Discovery 1 (2002) 859-866).

Amyloid-β plaques form, starting out from the so-called amyloid-β precursor protein (APP) which is an integral transmembrane protein (for which a physiologic function has not been clearly demonstrated either; however, the most recent research findings suggest that the APP acts as a so-called membrane cargo receptor for kinesin I). APP is proteolytically cleaved by so-called secretases, wherein physiologically mainly an Aβ peptide having a length of 40 amino acids ($A\beta_{40}$) is formed. Other, shorter and longer forms of Aβ also form, primarily also a version of 42 amino acids ($A\beta_{42}$) which exhibits a high aggregation ability. This $A\beta_{42}$-form therefore also is the predominant form in amyloid plaques. The secretases (α-, and primarily β- and gamma-secretases) responsible for these different cleavages therefore also are form primary targets aimed at by a possible AD treatment strategy. Therefore, it has been attempted to use modulators or inhibitors, respectively, for these enzymes in the treatment of AD (such as, e.g., benzodiazepines, sulphonamides, benzocaprolactames).

A further gene associated with AD is apolipoprotein E, and for this there exist three allele variants (APOE2, APOE3 and APOE4). It has been shown that persons with one or two copies of APOE4 have a higher risk of AD, whereas APOE2 carriers have a lower risk, compared with the total population. It has also been shown that persons who take statins, i.e. medicaments which inhibit the cholesterol biosynthesis, have a markedly reduced risk for AD. A further strategy for the treatment of AD therefore has been concentrated on the inhibition of cholesterol biosynthesis, such as with statins, e.g.

A further approach for the treatment of AD relates to the inhibition of the amyloid aggregation in cerebral plaques, which i.a. also could be carried out by secretase-inhibitors. Moreover, it has also been suggested to lower the zinc content, since zinc at physiologically relevant concentrations is capable of inducing the aggregation of Aβ.

Finally, also immunological strategies have been described, e.g. an immunization with $A\beta_{42}$, which, however, had to be stopped due to severe side effects within the scope of a clinical study (Willke, Bild der Wissenschaft, 9 (2003), 24-28).

Further AD treatment strategies which have been suggested in the prior art relate to the prevention of APP expression and to the increase in the Aβ clearance, wherein substances that interact with the APP promoter region have been searched for the former one. With regard to the Aβ clearance, an increase in the activity of certain proteases, such as the insulin-degrading enzyme and neprolysin, or the peripheral application of anti-Aβ-antibodies (De Mattos et al., PNAS 98 (15) (2001), 8850-8855) have been suggested. Finally, attempts have also been made to re-dissolve already existing amyloid plaques, e.g. by lowering the amyloid β-level in the serum of AD patients. In this context it has also been suggested to reduce the plaque deposits of β-amyloid proteins in the brain by apheresis methods (U.S. Pat. No. 6,551,266, wherein the removal of macromolecules having a molecular weight of more than 500 kD by apheresis is suggested), however, without this actually being shown for AD. Yet, the dissolution of already existing plaques in brain cells directly by apheresis methods is not possible (blood/brain barrier cannot be crossed by plaques, or by molecules with >500 kD).

Therefore, it has been the object of the present invention to provide a new treatment and prevention strategy for Alzheimer's Disease.

Accordingly, by the present invention an apheresis device is provided which comprises a solid carrier, which can be contacted with the blood or plasma flow and includes an amyloid-β precursor protein(APP)-binding receptor. With the present apheresis device, a purposeful clearance of APP or of APP degradation products, in particular of $A\beta_{40}$ or $A\beta_{42}$, can be carried out by means of apheresis in AD patients, or in patients who have a risk of AD. It has been known that there exists a dynamic equilibrium of $A\beta_{42}$ between the central nervous system (CNS) and the plasma. In the mouse model it could be demonstrated (DeMattos PNAS 2001, cf. above) that the peripheral application of anti-Aβ-antibodies has an influence on the CNS and plasma $A\beta_{42}$ clearance and reduces the $A\beta_{42}$ load in the brain, without the anti-Aβ-antibodies overcoming the blood/brain barrier. These results have been confirmed by Matsuoka et al. (Journal of Neuroscience 2003: 29-33) by the peripheral application of other $A\beta_{42}$-binding molecules (gelsolin and GM1). The process of the formation of the plaques in the brain thus can be prevented by trapping $A\beta_{42}$ in blood. In doing so, it is not critical whether the receptors in the apheresis device which are contacted with the patient's blood or plasma are specific for $A\beta_{42}$ or for other degradation forms of APP; it is only essential that APP and its (proteolytic) degradation products, in particular $A\beta_{42}$, are eliminated from the blood by this specific adsorption, so that a "wrong" protein degradation (i.e. to $A\beta_{42}$) will not occur. Thus, the present invention is based on an approach to an application of the apheresis that is entirely different from that of U.S. Pat. No. 6,551,266, i.e. it is based on the elimination of the potential plaque building blocks, and not of the plaques as such. Besides, the elimination of plaques by means of apheresis must be dismissed as an option right from the start as not effective for the treatment of AD, since the blood apheresis is not even able to reach the regions of plaque formation in the brain.

On the other hand, the apheresis according to the invention has the decisive advantage over methods which cause a depletion of Aβ within the body itself (such as e.g., in DeMattos et al., PNAS 98(15) (2001), 8850-8855 with peripheral anti-Aβ antibodies), that in the present case no autoimmune responses can be triggered. Moreover, according to the invention, no substances need to be supplied to the patient which are able of acting only in the body proper (possibly only after they have been transported to a certain site), but the pathogenic agent is selectively removed, i.e., the cause of the disease is specifically extracorporeally separated, without having to eliminate the reaction products in the body.

In doing so, according to the invention the existent and already known apheresis devices in all of their embodiments can easily be adapted to the present invention. In particular, when choosing the solid carrier (and the apheresis device), the medical-technical usefulness thereof should be considered. Such carriers, methods or devices have been described i.a. in WO 97/48483 A, in U.S. Pat. No. 5,476,715, 6,036,614, 5,817,528 or 6,551,266. Corresponding commercial apheresis apparatus i.a. are also marketed by the companies Fresenius, Affina, Plasmaselect, ASAHI, Kaneka, Braun, etc., such as, e.g., the LDL-Therasorb®, the Immunosorba®, the Prosorba®, the Globaffin®, the Ig-Therasorb®, the Immunosorba®, the Liposorba®, the HELP®, the DALI®, the bilirubin-bile acid absorber BR-350, the Prometheus® detoxication, the MARS®, the ADAsorb-System from Medicap or the Plasma FLO-System. All these systems—even though in their commercial form not primarily always aimed at the specific elimination of a single protein—may be adapted to the present invention without any problems by a person skilled in apheresis, e.g. as immunapheresis and/or by installing the inventive solid carrier (e.g. as a column) in the apheresis device.

Therefore, according to the invention, by "APP binding receptors" also all those substances are to be understood, which have an affinity to the ligand APP and its biological by-products, in particular $A\beta_{42}$, and which are capable of removing these polypeptides from the blood or plasma of AD patients or of persons having an AD risk. These APP- or $A\beta_{42}$-receptors, respectively, preferably may be (polyclonal or monoclonal) antibodies, proteins, peptides, gangliosides or nucleic acids.

Particularly preferred in this respect are anti-APP antibodies, anti-$A\beta_{40}$-antibodies or anti-$A\beta_{42}$-antibodies, APP-binding proteins, in particular gelsolin, apoJ or apoE, APP-binding peptides, APP-binding gangliosides, in particular $G_{M1}$, or APP-binding nucleic acids, in particular aptamers, or mixtures of these receptors.

Examples of such antibodies are 3D6 ($A\beta_{1-5}$), 2H3 ($A\beta_{1-12}$), 2G3 ($A\beta_{33-40}$), 21F12 ($A\beta_{33-42}$), 12H7 ($A\beta_{33-42}$) (Johnson-Wood et al., PNAS 1997:1550-1555), 10D5, 16C11 (Bard et al., Nature Medicine 2000:916-919), the antibodies described by DeMattos et al. (2001) (m266, m243) as well as antibodies of the same specificity. Such antibodies are obtained e.g. during the immunization of mammals with vaccine formulations containing APP, $A\beta_{42}$ or fragments or variants thereof, optionally followed by cell fusion and clone selection protocols (in case of monoclonal antibodies).

Gelsolin (Matsuoka et al. 2003, see above), apoJ and apoE (DeMattos et al., 2001, see above) are further examples of APP-binding protein receptors. $G_{M1}$ is an example of an APP-binding ganglioside receptor (Matsuoka et al., 2003, see above).

Further examples of APP-binding proteins are the CETP (cholesteryl-ester-transfer protein) and the ERAB protein (size of 261 aa; He et al., JBC 273 (17) (1998), 10741-10746; Lustbader et al., Science 304 (2004), 448-452; in particular aa 1-186, and 1-158, respectively). Examples of APP-binding peptides are the APP-binding fragments derived from the APP-binding proteins. Specific examples of APP-binding peptides are KTYNLKKGQT-C ("Peptide 4077"), GIAVASK-TYNLKKGQTHTLEDFQRVLDV (ERAB 93-120), SKTYNLKKGQTHT (ERAB 98-110), C-HQKLVFFAED ("Peptide 1323"), C-EVHHQKLVFFAEDVGS ("Peptide 1324"), C-HQKIVFFAED ("Peptide 1325") and FGFPE-HLLVDFLQSLS-C ("Peptide 1208") (and also all the other ERAB, CETP, or β-breaker fragments, respectively, which include the APP-binding regions) (in these peptides, the terminal cysteines are not part of the native protein sequence, but have merely been attached for coupling of the peptides).

Peptides as APP-binding receptors may be assembled of D- or L-amino acids or combinations of D and L-amino acids, and may optionally have been altered by further modifications, ring closures or derivatizations. Suitable peptide receptors for $A\beta_{42}$, e.g., may be provided from peptide libraries which are commercially available. Preferably, these peptides have a length of at least 5, preferably 6, amino acids, in particular at least 8 amino acids, preferred lengths being up to 11, preferably up to 14 or 20 amino acids. According to the invention, however, also longer peptides may be used without any problems as APP-binding receptors. Furthermore, oligomers (such as, e.g., polyethylene-imine and polylysine) are suitable as receptors.

For producing such APP-binding receptors, of course, also phage libraries, peptide libraries, e.g. produced by combinatorial chemistry or by means of high throughput screening techniques for the most varying structures, are suitable (cf. e.g. in Phage Display: A Laboratory Manual by Carlos F. Barbas (Editor), et al.; Willats W G, Phage display: practicalities and prospects. Plant Mol. Biol. 2002 December, 50(6): 837-54; http://www.microcollections.de/showpublications.php#). Besides phage libraries based on randomization, also such libraries which use ribosomal displays or the bacterial display are suitable. Appropriate libraries and methods for generating them are known to the person skilled in the art and have been described i.a. in US 2004/0110281 A, WO 00/72880 A and WO 02/059148 A.

Furthermore, also APP-binding receptors based on nucleic acids ("aptamers"; yet also "decoy"-oligodeoxynucleotides (ds oligonucleotides which, on account of their sequence, constitute binding sites for transcription factors) can be employed, wherein also the latter can be found with the most varying (oligonucleotide-) libraries (eg. with 2-180 nucleic acid residues) (e.g. Burgstaller et al., Curr. Opin. Drug Discov. Dev. 5 (5) (2002), 690-700; Famulok et al., Acc. Chem. Res. 33 (2000), 591-599; Mayer et al., PNAS 98 (2001), 4961-4965, and many others). The nucleic acid backbone may, e.g, be formed by the natural phosphorodiester compounds, but also by phosphorothioates or combinations or chemical variations (e.g. as PNA), wherein, according to the invention, as the bases primarily U, T, A, C, G, H and mC may be used. The 2'-residues of the nucleotides which can be used according to the present invention, preferably are H, OH, F, Cl, $NH_2$, O-methyl, O-ethyl, O-propyl or O-butyl, it also being possible for the nucleic acids to be otherwise modified, i.e. provided with protective groups, e.g., such as commonly employed in oligonucleotide synthesis. Therefore, APP-binding aptamers are also preferred APP-binding affinity molecules within the scope of the present invention.

The aptamers for APP are found by means of the method described hereinafter, e.g. Immobilized APP (or another one of the above-described forms) is contacted with a mixture of nucleic acids, wherein highly affine binding nucleic acids are separated from the less affine binding nucleic acids or from those which do not bind at all. The mixtures with nucleic acids are typically nucleic acid libraries which have been prepared e.g. by combinatorial chemistry. A nucleic acid library contains a plurality of mutually different nucleic acids, wherein at least in a partial sequence region a randomization (with natural and/or non-natural nucleotides) is furnished. A conserved sequence region can, but need not be provided. Randomization in n positions with m different nucleotides will give rise to a library with $n^m$ elements.

For locating the APP-specific affinity nucleic acids, the following steps are carried out. a) A column (inwardly) is loaded with APP (etc.), and APP (etc.) is immobilized in the column; b) the mixture of nucleic acids is applied to a first end of the column, a defined volume flow of carrier substance, which runs through the column from the first end to the second end of the column, being furnished; c) the nucleic acids are bound and immobilized with decreasing affinity of the nucleic acids to APP (etc.) at an increasing distance from the first end of the column; d) the volume flow of carrier substance through the column completed after a defined run-ning time; e) the column is separated by several partitions into column segments, each segment receiving an associated run-path coordinate; f) from at least one segment, the immobilized nucleic acids are non-specifically desorbed and recovered by allocation of the run-path coordinate associated with that segment. The expression "inwardly of the column" means within a lumen quite generally. The expression "column" should comprise all types of solid carrier systems, also not completely enclosed carrier systems are possible.

The immoblization of APP (etc.) may be effected according to the conventional methods of column chromatography. As column, any mechanical construct is to be denoted which has a lumen with two ends. As structure material, all the materials common for columns, such as metals, glass and/or synthetic materials, are possible. The column may inwardly be provided with an APP-(etc.) binding matrix and/or the structure material may be suitable or have been prepared for a direct binding of the target molecules. A mixture of nucleic acids denotes nucleic acid libraries having a number of typically $10^6$ to $10^{22}$/Mol, in particular $10^{10}$ to $10^{21}$/Mol, mutually different nucleic acid species. In the library which is applied to the column, each nucleic acid species statistically is represented for instance by 10 to $10^{17}$, in particular 100 to $10^{13}$, molecules. The carrier substance usually is a liquid in which the nucleic acid library is soluble and stable. For this, all the buffers and the like which are common for nucleic acid libraries are suitable. The volume flow of carrier substance can be adjusted prior to application of the nucleic acid library. Then the nucleic acid library is added to the carrier substance flow at the input side of the column. The nucleic acid library may, however, also be directly applied. After a run-time which is determined by the set-up of the column and by the volume flow adjusted, the "plug", which has been applied by the nucleic acid library, leaves again at the output side of the column (widened by folding with the diffusion), bound nucleic acids having been separated from the "plug" and immobilized in the column. Suitably, the volume flow through the column is adjusted to be little or non-turbulent, preferably laminar (sum of the acceleration vectors of the carrier substance over the column volume, in particular over the column cross-section, is minimal, ideally 0). The total number of the APP molecules in the column typically will be the $10^2$ to $10^{16}$-fold, in particular the $10^3$- to $10^{15}$-fold, of the number of nucleic acid molecules of an individual species in the nucleic acid library applied. The binding of the nucleic acids to the APP molecules preferably occurs under conditions which correspond to a later use of the nucleic acids during the apheresis, e.g. in a suitable buffer which is appropriately adapted in terms of temperature, ionic strength, pH and buffer conditions. The carrier substance as well as the solvent of the nucleic acid library are then to be chosen accordingly with regard to the components thereof. Separation of the column into a plurality of column segments may, e.g., be effected by cutting the column into parts, said cuts preferably being orthogonal to the volume flow vector. Yet, the column may also previously have been assembled of column segments, wherein one column segment tightly adjoins the next column segment, preferably in the direction of the volume flow vector (assembling cross-section orthogonal to the volume flow vector). Then the separation may be effected by releasing the previously formed composite of column segments. The non-specific desorption may be effected by elution with a sufficiently strong ligand by displacement, complexing, modification and/or destruction of APP, physico-chemically or thermally. Also mechanical processes, e.g. ultrasonics, may be employed for desorption or for enhancing the desorption. Also combinations of the previously mentioned desorption methods may be used. It goes without saying that the nucleic acids must not be decomposed by the desorption method used.

The above-described steps are based on the finding that a nucleic acid library can be separated in analogy with a protein mixture by means of affinity chromatography spatially in accordance with the affinity to the target molecule, in the case described here, for APP (etc.). The invention furthermore is based on the finding that a mixing of desorbing nucleic acids of various affinities, occurring by means of non-specific desorption, can be avoided in that prior to the non-specific desorption, the column, with the nucleic acids bound therein, practically is divided into affinity sections, and in that the nucleic acids bound in the thus-obtained affinity sections, or column segments, respectively, can be easily and non-specifically desorbed without an interfering ligand coupling, e.g. within the scope of a PCR or an RT-PCR, and can also be non-specifically amplified. Subsequent selection artifacts are avoided. Neither are ligands, in particular high concentrations of ligands, required for desorption. Finally, practically all the bound and subsequently desorbed nucleic acid molecules are available for an amplification. This makes it possible to work with low nucleic acid concentrations. Basically, it is already sufficient if, in the statistic average, every species in the nucleic acid library is represented by one molecule. If the number of APP molecules in a column segment is statistically 1, then even single nucleic acid species can be separated according to their affinity to the target molecule.

A particular advantage of this method will be explained hereinafter. Separation of the nucleic acids according to affinity results in that nucleic acids in one column segment have a similar affinity with different specificity (different regions of APP are bound by, or are binding sites for, respectively, the APP affinity nucleic acids).

Basically, it suffices if one segment, to which a desired affinity is allocated, (isolatedly) is further processed for desorption. A prerequisite for this is, however, to have an idea of the affinity distribution in the nucleic acid library applied—except in case of maximum affinity, wherein the, in relationship to the volume flow vector, first column segment is further processed. Therefore, as a rule it is preferred that the immobilized nucleic acids of each segment can be separately desorbed and recovered, with a respective allocation of the runpath coordinates of each segment to the nucleic acids recovered therefrom.

Basically, any type of desorption is possible. Preferably, the non-specific desorption is carried out by means of conventional physico-chemical or thermal methods. Thermal desorption is effected by heating the column segment, or the solution contained therein, respectively. Heating may be by electrical heating or by irradiation with microwaves or by IR, respectively. The heating techniques from PCR technology are particularly suitable. Besides the amplification of nucleic acids, or aptamers, respectively, by means of polymerase, also other amplification methods may, of course, be used, such as, e.g., by means of ligase. The non-specific desorption may be assisted by chemical modification of APP, e.g. oxidation by sodium periodate or the like, or by non-specific complex formation, e.g. by means of borate or the like, to block cis-trans diol bonds in carbohydrates.

Therefore, it is preferred if the non-specific desorption is carried out by thermal desorption in a, preferably extended, high temperature phase of a PCR or of an RT-PCR. With this, a synergy effect is achieved, since as a rule, in particular when working with nucleic acid libraries at low concentrations of the nucleic acid species, an amplification is required anyway. To increase the yield, it is worked e.g. with 5 to 60, preferably with 20 to 60, most preferably with 45 to 55 cycles. Within the scope of the amplification, it is possible to work with at least one labeled primer. The primer may have at least one endonuclease cleavage site. Such a cleavage site serves e.g. to free the amplified material from larger regions of the primer sequence. The nucleotide building blocks, be it within the primer or in the nucleic acids to be selected, may, e.g., be labeled by fluorescence dyes. As the fluorescence dyes, mention may be made for instance, of Alexa™ Fluorine 488, Fluorine 532, Fluorine 546, Fluorine 568, Fluorine 594, Oregon Green 488, Fluoresceine, Rhodamine 6G, Tetramethylrhodamine, Rhodamine B and Texas Red. The amplified material may also be labeled by two different chemical modifications at different ends, as long as the groups introduced during the modification are suitable so that they can be bound as ligands to a different affinity matrix each.

For the reliable separation of non-affine or low-affine nucleic acids, it is recommendable to introduce washing method steps between suitable method stages. In particular, it is preferred if at least one washing method step is carried out between the method steps d) and e). For washing, e.g. the solvent, or the medium of the nucleic acid library, or the carrier substance, respectively, is suitable.

It is preferred if the inward coating of the column with APP (etc.) and its immobilization is carried out by covalent binding, preferably after activation with chemically highly reactive groups (e.g. tresyl chloride, cyanobromide and/or periodate), or via bifunctional spacer links after modification with chemically little reactive groups (e.g. amine, hydroxy, keto and/or carboxyl). Examples of the spacer backbone for suitable spacer links are: substituted and unsubstituted $C_2$-$C_{10}$ alkyl groups, substituted and unsubstituted $C_2$-$C_{10}$ alkenyl groups, substituted or unsubstituted $C_2$-$C_{10}$ alkynyl groups, substituted and unsubstituted $C_4$-$C_7$ carbocycloalkyl groups, substituted and unsubstituted $C_4$-$C_7$ carbocycloalkenyl groups, substituted and unsubstituted $C_7$-$C_{14}$ aralkyl groups, a heterocyclic molecule with hetero atoms selected from nitrogen, oxygen, sulfur, wherein said substitutions may consist of alkyl, alkenyl, alkynyl, alkoxy, thiol, thioalkoxy, hydroxyl, aryl, benzyl, phenyl, nitro, halogen, ether groups with 2 to 10 carbon atoms and 1 to 4 oxygen- or sulfur atoms, polyalkylglycol, halogen, hydroxyl, thiol, keto, carboxyl, amides, ether compounds, thioether, arnidine derivatives, guanidine derivatives, glutamyl derivatives, nitrate ($ONO_2$), nitro ($NO_2$), nitrile, trifluoromethyl (—CF3), trifluoromethoxy (—$OCF_3$), O-alkyl, S-alkyl, NH-alkyl, N-dialkyl, O-aralkyl, S-aralkyl, NH-aralkyl, amino, azido ($N_3$), hydrazino ($NHNH_2$), hydroxylamino ($ONH_2$), sulfoxide (SO), sulfone ($SO_2$), sulfide (S—), disulfide (S—S), silyl. Typically, spacer links are bifunctional, wherein the functionalities may be equal or different and are selected, for instance, from the group consisting of "N-hydroxysuccinimide and hydrazides".

To reduce the variety within the nucleic acids obtainable from one column segment, it is preferred if each column segment, in its statistic average, contains from 0.1 to $10^3$, preferably from 1 to $10^2$, most preferably from 1 to 10, APP (etc) molecules. In correlation therewith, the nucleic acid library as applied, in its statistic average may contain from 0.1 to $10^3$, preferably from 1 to $10^2$, most preferably from 1 to 10, nucleic acid molecules of one species.

For the structure material of the column, basically all the materials known from affinity chromatography may be used. Among them are columns of silica gel or polymers, such as polyethylene after activation by chemical derivatization or plasma activation. The length of the column segments suitably is within a range of from 0.1 µm to 1 mm, preferably 0.1 to 100 µm, most preferred 0.5 to 10 µm. Such sections can easily be made, e.g. by means of a microtome. The inner diameter of the column suitably is in a range of from 0.05 to 1 mm, preferably from 0.1 to 0.5 mm, most preferred from 0.2 to 0.4 mm.

It is suitable if undesired nucleic acids are eliminated before the separation proper (binding or mechanical separation) of the nucleic acids. Undesired nucleic acids are, e.g., nucleic acids which bind to APP-free inner surfaces of the column. Then, an APP-free column can be provided upstream, and the nucleic acid library can be guided therethrough beforehand.

With the previously described types of methods, working may be continuous, i.e. for instance by consecutively connecting columns, or discontinuous, e.g. by an intermediate collection of the eluent from the preceding column.

To obtain a further improvement of the affinity separation, basically it can be proceeded in various ways. Thus, the nucleic acids desorbed from one or several segments, optionally after amplification, may repeatedly be subjected to the inventive methods, and/or the elutropy of the conditions during the desorption may be increased (temperature, ionic strength, pH, buffer conditions). Alternatively, the spatial density of APP and, consequently, of the bound nucleic acids, i.e. the number of the APP molecules, in a column segment may be reduced.

APP-binding aptamers (which, according to the invention as defined above, also include $A\beta_{42}$-binding aptamers) therefore are also preferred APP-binding receptors within the scope of the present invention.

According to the invention, therefore, the APP-binding receptors which, preferably, are comprised of peptides, antibodies or nucleic acids, are used on a suitable carrier material for the extra-corporeal elimination of APP and its proteolytic degradation products in Alzheimer (risk) patients.

When using the present invention in the medical routine practice, it is necessary that the carrier is sterile and pyrogen-free, so that any carrier substance, or any receptor/carrier combination which meets these requirements is preferred according to the invention (cf. e.g. U.S. Pat. No. 6,030,614 or U.S. Pat. No. 5,476,715). Among the suitable examples are porous homopolymers, co- or ter-Polymers of vinyl containing monomers (e.g. acrylic acid, such as, e.g., TSK Toyopearl, Fractogel TSK), carriers with modifications (activations) with oxirane containing compounds (e.g. epichlorohydrin) and, optionally, further reactions with $NH_3$, amino or carboxyl containing compounds, or CNBr or CNCl adsorbing agents, as described in EP 110 409 A and DE 36 17 672 A. Particularly preferred adsorption materials for therapeutic purposes are suitable to prevent a loss of blood cells, do not activate the complement system or do so only slightly, and prevent aggregate formation in the extracorporeal circulation as far as possible. Furthermore, the carrier materials used, preferably should be sufficiently stable relative to sterilizing procedures also when coupled to receptors, in particular relative to ethylene-oxide saturation, glutaraldehyde saturation, gamma-irradiation, vapor treatment, UV treatment, solvent treatment and/or detergent treatment, etc. Also products based on sepharose, agarose, acryl, vinyl, dextrane, etc. may, e.g., be employed which, preferably, comprise suitable functional groups for binding of the APP-binding receptors already in their commercially available form. Further suitable carriers also include monoliths (carriers based on cross-linked glycidyl-methacrylate-co-ethylene glycol dimethacrylate-polymer) Supol (Poschalko et al., J. Am. Chem. Soc. 2003 Nov. 5; 125 (44): 13415-26).

For coupling the receptors to the suitable carriers, the chemistry known to the person skilled in the art (e.g. Bioconjugate Techniques, Greg T. Hermanson, Ed., Academic Press Inc., San Diego, Calif., 1995, 785 pp.) can be used.

In a further aspect, the present invention relates to the use of the inventive device for providing a treatment or for providing a treatment arrangement of Alzheimer's Disease, or for preventing such a disease, by suitably preparing the device for the treatment of the respective patient. When carrying out the treatment, a patient is connected to the apheresis apparatus for a period of time sufficient to effectively eliminate APP polypeptides, wherein the patient's blood or plasma flow is contacted with the solid carrier that comprises the APP-binding receptor, whereupon APP and/or the proteolytic degradation products of APP, in particular $A\beta_{42}$, are bound. In the course of the apheresis treatment, of course, a peripheral or central-venous vein access or arteriovenous fistula must be ensured, just as a sufficient anticoagulation, and also the required quantification and measurement data have to be recorded. Moreover, in most apheresis methods, a primary separation of plasma and blood cells will be required prior to the plasma treatment proper. Particular persons in whom a preventive measure will be required are persons with familial affliction, elderly persons (>50, >60 or >70 years) or persons with another risk factor for AD, in particular genetic factors.

The invention will be explained in more detail by way of the following Examples as well as by the drawing figures to which, of course, it is not restricted.

Therein,

Figure 1:
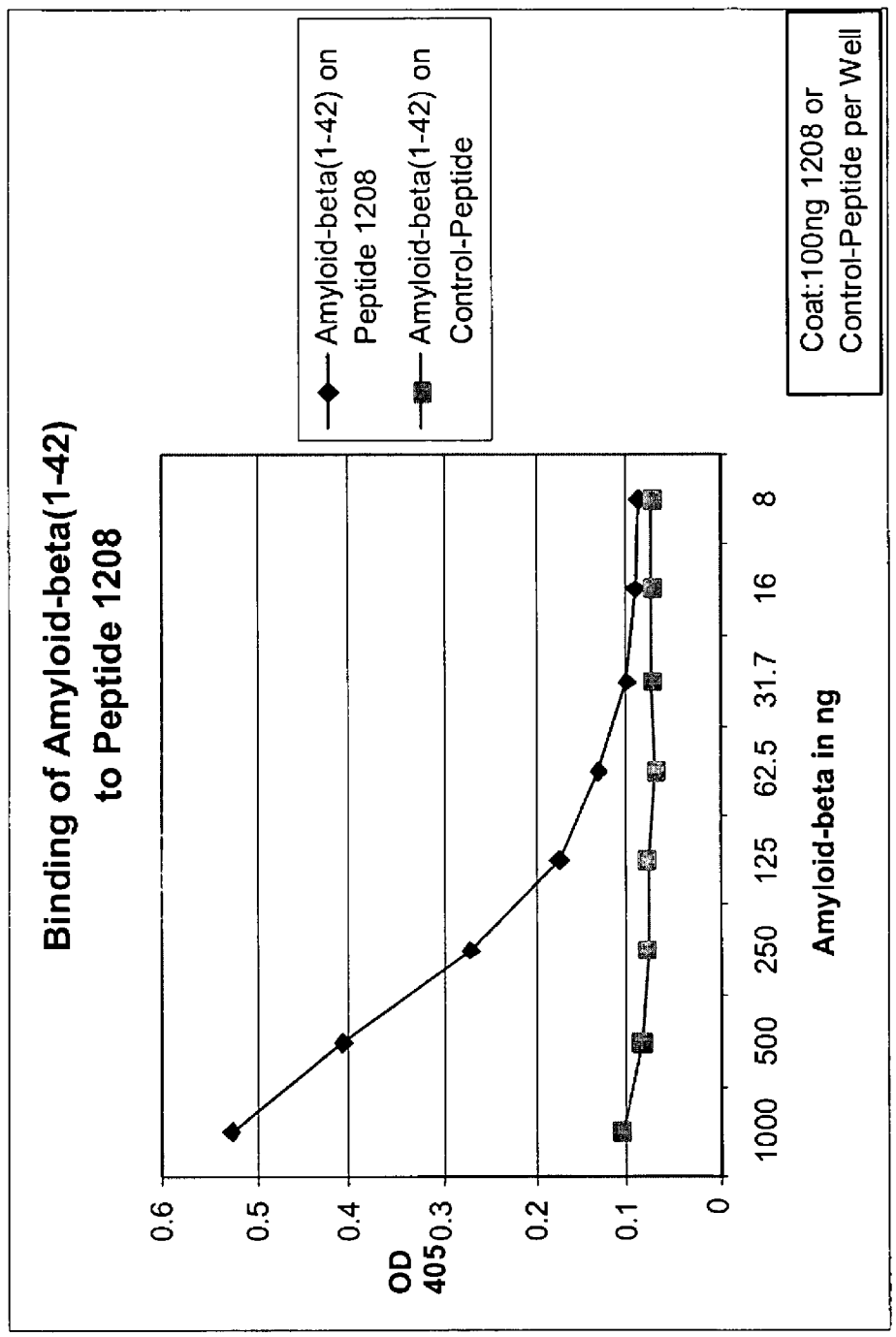
FIG. 1 shows the binding of $A\beta_{42}$ to peptide 1208 (coupled to BSA and coated to an ELISA plate)

1. Production of the APP Receptor Carrying Carrier 1.1 Monolithic Column

A CIM® Epoxy Monolithic column (BIA Separations, SI) is equilibrated with 0.5 m Na phosphate buffer at pH 8.0 according to the producer's instructions, and a monoclonal antibody against Aβ peptide is activated, also according to the producer's instructions, and coupled to the CIM column. The column is washed several times with phosphate buffer (+1 M NaCl), and epoxy groups in excess optionally are blocked.

Quality assurance is carried out by checks in the washing and equilibrating eluate; only acids without active epoxy-groups and without antibody leakage in the eluate are used further on and installed in an apharesis apparatus.

1.2 Sepharose Column

An agarose bulk material (Sepharose CL4B) is aseptically filled into a sterile and pyrogen-free container, and the material is aseptically washed, the gel material being completely dried under vacuum between each washing step. Subsequently, the Sepharose is vapor-sterilized for 30 minutes at 115° C. in the autoclave.

After the sterilisation, the Sepharose is taken up in a sterile container in 60% acetone/water and activated with CNBr and triethylamine (14 g of CNBr per 96 ml of acetone; 30 ml of triethylamine in 66.2 ml of 87% acetone). Then an acetone/HCl solution was added (392 ml of sterile, pyrogen-free water; 16.3 ml of 5N HCl, 408 ml of acetone). The activated Sepharose is washed and supplied to the coupling reaction within 2 h so as to prevent hydrolysis of activated groups.

A sterile-filtered antibody solution (m266, and m243, respectively), is introduced into the reaction vessel and stirred for at least 90 min. Finally, the reaction solution is washed thoroughly (with isotonic phosphate buffer), until no reaction products are detectable in the eluate, and the antibody-coupled Sepharose is filled into sterile and depyrogenized glass columns with glass sintering and subjected to a final quality check (eluate analysis with regard to reaction products, heavy metals etc.; particle analysis, pyrogenicity; sterility).

2. Animal Model for the Apheresis Treatment of Alzheimer Patients

In the institute for diabetes "Gerhardt Katsch", a miniaturized extracorporeal system has been developed for applying the apheresis therapy in the small animal model rat. Worldwide, such apheresis test systems are available to a very limited extent only. The repeated apheresis treatment on the same test animal and subsequent examinations in the follow-up period for evaluating the success of the therapy are quite new and so far have not been described in international publications.

Apheresis is an alternative therapeutic method in which pathogenic substances are withdrawn from blood externally of the body. In human medicine, the apheresis so far has been used for the treatment of more than 100 diseases. With the help of apheresis, disease-relevant substances could completely or at least partially be removed from the blood i.a. in autoimmune diseases, such as rheumatoid arthritis, myasthenia gravis, endocrinal ophthalmopathy, Multiple Sclerosis, systemic Lupus erythematosis, Stiff-Man Syndrome and Diabetes Type 1. Hitherto, however, apheresis has only been accepted as an alternative method for the treatment of therapy-resistant chronic diseases that involve great burdens on and a marked reduction in the quality of life of the affected patients. A substantial reason for this is that so far there has been no detailed knowledge regarding the mechanism of action of a successful apheresis therapy.

By using acknowledged animal modes, such as, e.g., for Diabetes type I and rheumatoid arthritis, both, a further clarification of the mechanisms of action of the apheresis method is possible and novel indications for the apheresis treatment can be tested preclinically. To carry out apheresis treatments, the test animals first are provided with chronic vascular catheters. In the extracorporeal circulation, the plasmatic and cellular components of the blood subsequently are separated by plasma filters. While the cellular components immediately return to the animal, the plasma can be purified by various adsorption methods (immunoadsorption and others) before being returned. The good tolerance of such repeated apheresis treatments has already been proven for different rat strains (body mass, hematocrite, general condition). The apheresis test system has been tested with animals having a minimum weight of 250 g, and has been used in rat models for autoimmune diseases (Diabetes type I, collagen Type II-induced arthritis).

The extracorporeal system for plasmapheresis in the small animal model may be used for different types of adsorption. The use of this test system in models for chronic diseases allows for (A) the testing of new treatment and prevention strategies, (B) the elucidation of the mechanisms of action of different apheresis technologies, and (C) the determination of the indications for individual apheresis therapy methods. The IDK is the competent partner in the pre-clinical testing of newly developed apheresis methods and can essentially contribute to the transition and marketing of new therapeutic methods from the development phase via the testing in the animal experiment up to their clinical application in patients (http://www.praeklinik.de/).

Before the experimental apheresis therapy is started, the animals are provided with arterial and venous catheters, or chronically catheterized rats (vascular catheters which are suitable for the application of test substances and for drawing blood samples as well as for carrying out the apheresis therapy and the clamp examinations in the animal model) are used. In apheresis, initially blood cells and plasma are separated by means of plasma filters in a first step. While the blood cells are immediately re-infused into the animal (via the venous catheter), the separated plasma is guided past the adsorption means prepared in Example 1 (wherein the ligands are separated from the plasma by binding to the immobilized affinity peptides), before it is returned into the animal.

3. $A\beta_{42}$ Aptamers 3.1 Activation of a Silica Gel Column with Tresyl Chloride The column is rinsed with acetone. For the activation, an anhydrous solution (2 ml of acetone, 1 ml of tresyl chloride, a few drops of pyridine) is passed through the column (10-fold column volume) and it is incubated on ice over night. Subsequently, the column is rinsed with the 20-fold column volume of 100% acetone (anhydrous). The activated column can be stored in 1 mM HCl.

3.2 Activation of a Polyethylene Column

At room temperature, a polyethylene tube is rinsed with the 20-fold column volume of a solution (2% potassium permanganate ($KMnO_4$) (w/v) in concentrated sulfuric acid ($H_2SO_4$)), and then with distilled water. For further coupling of the column surface, bivalent or polyvalent molecules can be used for cross-linking, which have at least one reactive aldehyde group (e.g. 1% glutaraldehyde). They are passed through the column for 1 h at 4° C. Subsequently, the reaction is stabilized by reducing conditions (e.g. by sodium cyanoborohydride (0.00025% w/v in 0.15 M NaCl, pH 3.9).

3.3 Coupling of $A\beta_{42}$ to the Activated Silica Gel Column

The tresyl chloride-activated column is rinsed with 0.1 M $Na_2CO_3$ (pH 8.5). For coupling, a peptide or protein (2 mg/ml 0.1 M $Na_2CO_3$, pH 8.5) is passed through the column several times for 2 h at 37° C. and subsequently on ice for 4 h. To block free binding sites of the column, subsequently an excess of 0.2 M glycine, pH 8, is passed through the column.

3.4 Coupling of a Glycoprotein to the Activated Polyethylene Column

The activated column is rinsed with 0.1 M $Na_2CO_3$ (pH 8.5). For coupling purposes, $A\beta_{42}$ (2 mg/ml, 0.1 M $Na_2CO_3$, pH 8.5) is passed through the column several times for 2 h at 37° C. and subsequently for 4 h on ice. To block free binding sites of the column, subsequently an excess of 0.2 M glycine, pH 8, is passed through the column. To improve the reaction, 1-ethyl-3-(3-dimethylaminopropyl)-carbodiimide (EDC), 5% w/v, may be added.

3.5 Production of a Column for Eliminating Undesired Molecules

The tresyl chloride-activated column is rinsed with 0.1 M $Na_2CO_3$ (pH 8.5). If the elimination is to be directed against a molecule having one or several primary or secondary amines, this molecule, or the mixture (2 mg/ml 0.1 M $Na_2CO_3$, pH 8.5) is passed through the column several times over night at RT. For blocking free binding sites of the column, subsequently an excess of 0.2 M glycine, pH 8, is passed through the column. If no elimination against certain molecules with one or more primary or secondary amines is desired, all the binding sites of the column are blocked with glycine.

Further derivatization methods can be found in the following references, e.g.: Patterson, W. J., National Aeronautics and Space Administration, Technical Memorandum, NASA TMX-73311, U.S. Government Printing Office, Washington, D.C., 1976, Ma, S. M., Gregonis, D. E., von Wagenen, R. A., and Andrade, J. D., in "Hydrogels for Medical and Related Applications" (J. D. Andrade, Ed.), Amer. Chem. Soc. Symp.

Series, Vol. 31, p. 241, 1976, Harris, J. M., Struck, E. C., Case, M. G., Paley, M. S., Van Alstine, J. M., and Brooks, D. E., J. Polymer Sci., Polymer Chem. Ed., 22, 341 (1984), Regnier and Noel, Regnier, F. E., and Noel, R. J., J. Chromatog. Sci., 14, (1976), Yalpani, M. and Brooks, D. E., J. Polymer Sci., Polymer Chem. Ed., 23, 395 (1985).

3.6 Carrying Out the Contact of the Nucleic Acids on $A\beta_{42}$ and Separation of the Column.

The coated columns are connected in series without leakage, first the columns for eliminating undesired molecules, subsequently the $A\beta_{42}$ column. For equilibration purposes, a suitable buffer, e.g. a buffer solution (10 mM Tris-HCl, 50 mM KCl, 1.5 mM $MgCl_2$ and gelatin 0.001% (w/v) pH 8.3) are passed over the column for 1 h on ice. The nucleic acids of the combinatorial nucleic acid library are taken up in 1 ml of the same buffer and heated to 95° C. for 10 min for melting of double strands, and then they are passed over the column several times (4-30 times). Then the columns are separated and washed on ice over night with the chosen buffer (see above). The separation of the column in flow direction was effected with a suitable cutting tool.

4. Binding Studies of $A\beta_{42}$ on Peptide 1208 (FGFPE-HLLVDFLQSLS-C)

For an analysis of the amyloid-beta-binding to peptide 1208, at first the peptide was coupled to a carrier protein (BSA), with the peptide concentration being 500 µMol (approximately 1 mg/ml). The 1208-BSA conjugate was bound to an ELISA plate, wherein 100 ng of peptide were bound per well. The ELISA plate was saturated with PBS, 1% BSA, and subsequently, the binding of amyloid-beta (1-42) was analyzed in a concentration range of 8-100 ng/well. Bound amyloid-beta was detected with a specific mouse antibody. Finally, the amount of bound amyloid-beta was quantified with the help of a biotinylated anti-mouse antibody and Streptavidin-coupled peroxidase. As the substrate, ABTS was used, and the analysis was carried out in an ELISA Reader at a wave length of 405 nm (FIG. 1).

Figure 2:
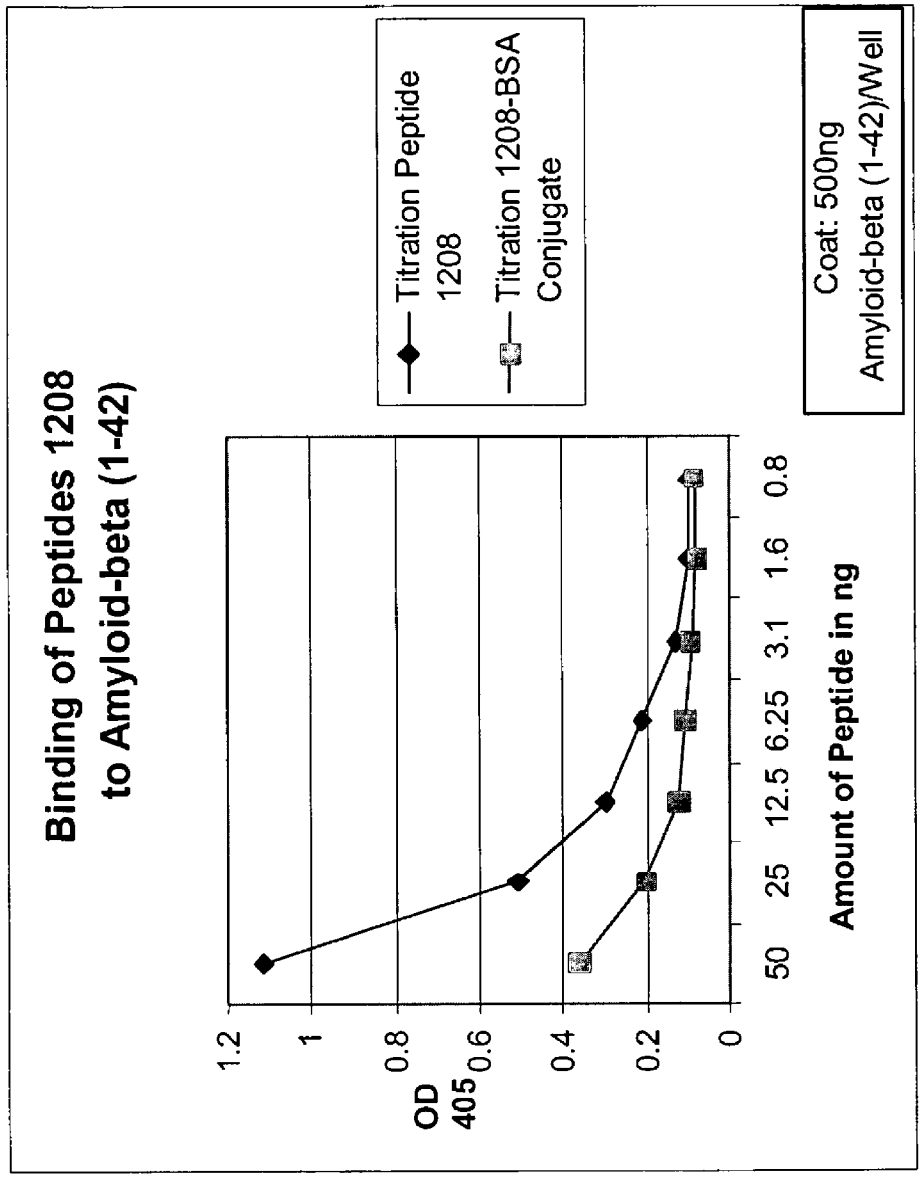
FIG. 2 shows the binding of peptide 1208 (and 1208-BSA) to $A\beta_{42}$ (coated to ELISA plate)

For the analysis of the binding of peptide 1208, amyloid-beta (1-42) was bound to an ELISA plate (500 ng per well). Subsequently, the ELISA plate was saturated with PBS, 1% BSA, and then free peptide 1208 or 1208-BSA conjugate, respectively, was added (1.6-50 ng). Bound peptide was detected with a specific monoclonal antibody. For the final quantification, a biotinylated anti-mouse antibody and Streptavidin-coupled peroxidase were used. As the substrate, ABTS was used, and the analysis was carried out in an ELISA Reader at a wave length of 405 nm (FIG. 2).

Figure 3:
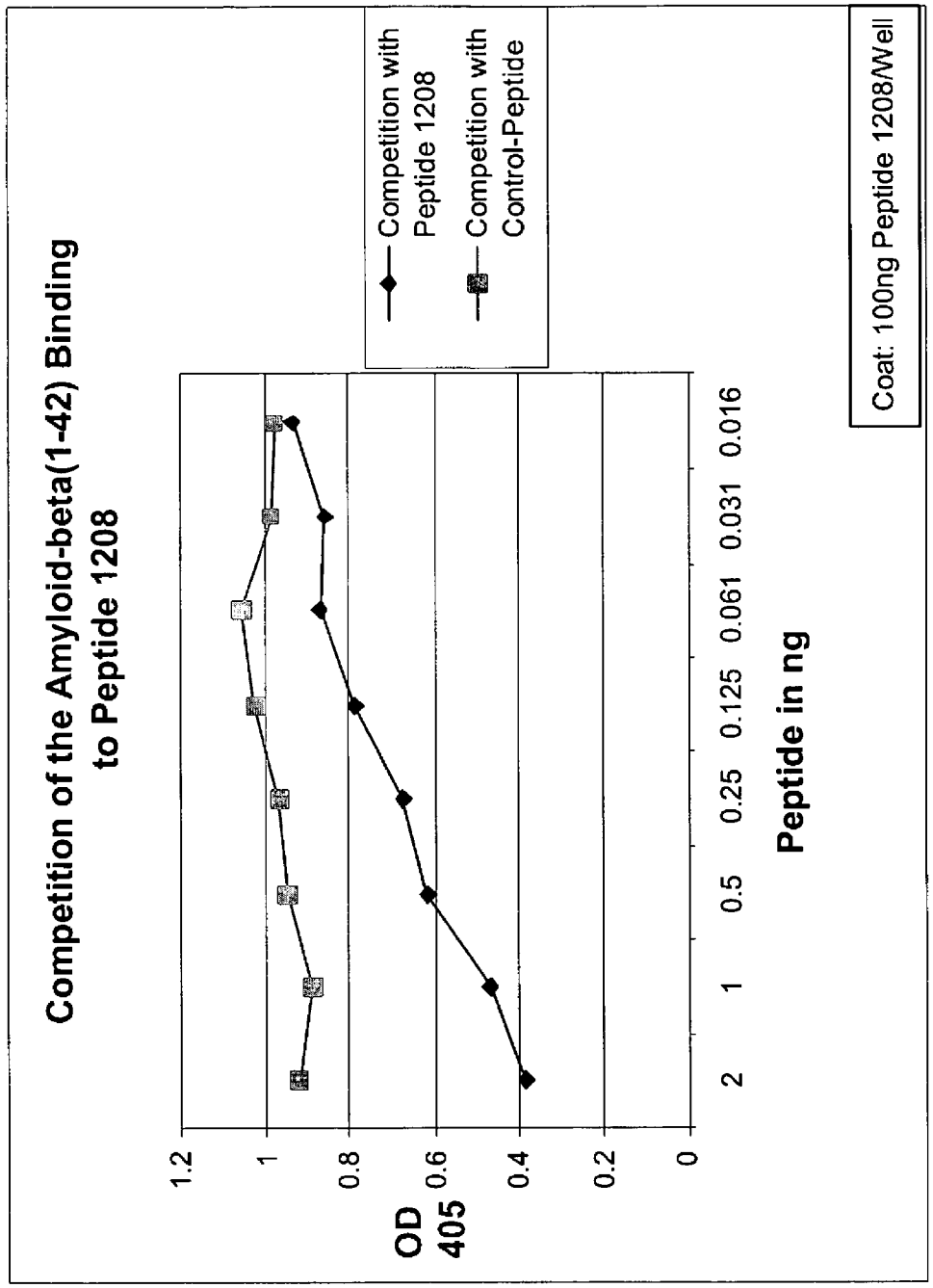
FIG. 3 shows the competitive binding of $A\beta_{42}$ to 1208-BSA.

1208-BSA conjugate was bound to an ELISA plate (100 ng of peptide per well), and the plate was saturated with PBS, 1% BSA. Subsequently, the binding of amyloid-beta (1-42) (100 ng/well) in the presence of free peptide 1208 or of control-peptide (concentration range 30-2000 ng/) was analyzed. The detection of the bound amyloid-beta was as described before (FIG. 3).

The invention claimed is:

1. A method for treating Alzheimers Disease (AD) in a patient suffering from or at risk for AD, the method comprising
contacting blood or plasma flow of a patient suffering from AD or a patient with a risk for AD with an apheresis device, the apheresis device comprising a solid carrier, said solid carrier having anti-amyloid-β precursor protein (APP) antibodies attached to a surface of the solid carrier, and wherein contacting with the apheresis device is for a time sufficient to reduce APP polypeptides in the brain and treat AD in the patient.

2. The method according to claim 1, wherein the anti-APP-antibodies are anti-Abeta40 antibodies or anti-Abeta42 antibodies.

3. The method according to claim 1, wherein the anti-APP-antibodies are anti-Abeta40 antibodies.

4. The method according to claim 1, wherein the anti-APP-antibodies are anti-Abeta42 antibodies.

5. The method according to claim 1, wherein the carrier is a sterile and pyrogen-free column.

6. The method according to claim 1, wherein the method comprises contacting blood or plasma flow of a patient suffering from AD.

7. The method according to claim 1, wherein the method comprises contacting blood or plasma flow of a patient with a risk for AD.

* * * * *